(12) United States Patent
Schelling et al.

(10) Patent No.: US 8,748,655 B2
(45) Date of Patent: Jun. 10, 2014

(54) PROCESS FOR PREPARING LIGHT-COLOURED ISOCYANATES OF THE DIPHENYLMETHANE SERIES

(75) Inventors: Heiner Schelling, Kirchheim (DE); Jon S. Speier, Baton Rouge, LA (US); Eckhard Stroefer, Mannheim (DE); Byoung-Yeon Kim, Baton Rouge, LA (US)

(73) Assignee: BASF SE, Ludwigshafen (DE)

(*) Notice: Subject to any disclaimer, the term of this patent is extended or adjusted under 35 U.S.C. 154(b) by 91 days.

(21) Appl. No.: 13/383,433

(22) PCT Filed: Jul. 7, 2010

(86) PCT No.: PCT/EP2010/059684
§ 371 (c)(1),
(2), (4) Date: Mar. 21, 2012

(87) PCT Pub. No.: WO2011/006807
PCT Pub. Date: Jan. 20, 2011

(65) Prior Publication Data
US 2012/0172620 A1 Jul. 5, 2012

Related U.S. Application Data

(60) Provisional application No. 61/225,376, filed on Jul. 14, 2009.

(51) Int. Cl.
*C07C 263/10* (2006.01)
(52) U.S. Cl.
USPC .......................................................... 560/347
(58) Field of Classification Search
USPC .......................................................... 560/347
See application file for complete search history.

(56) References Cited

U.S. PATENT DOCUMENTS

| | | | |
|---|---|---|---|
| 3,660,261 A | 5/1972 | Wright et al. | |
| 5,693,853 A * | 12/1997 | Abrahamsson | 560/347 |
| 6,576,788 B1 | 6/2003 | Penzel et al. | |
| 6,900,348 B1 | 5/2005 | Reif et al. | |
| 7,368,595 B2 * | 5/2008 | Wershofen et al. | 560/347 |
| 2004/0024244 A1 | 2/2004 | Walsdorff et al. | |
| 2007/0276154 A1 | 11/2007 | Haas et al. | |
| 2010/0217035 A1 | 8/2010 | Knoesche et al. | |
| 2011/0124908 A1 | 5/2011 | Rumpf et al. | |
| 2011/0251425 A1 | 10/2011 | Penzel et al. | |
| 2011/0263892 A1 | 10/2011 | Breuninger et al. | |

FOREIGN PATENT DOCUMENTS

| | | |
|---|---|---|
| EP | 0 876 335 | 11/1998 |
| WO | 99 54289 | 10/1999 |
| WO | 01 00569 | 1/2001 |
| WO | 2009 013303 | 1/2009 |

OTHER PUBLICATIONS

International Search Report Issued Nov. 2, 2011 in PCT/EP10/59684 Filed Jul. 7, 2010.
U.S. Appl. No. 13/256,541, filed Sep. 14, 2011, Mattke, et al.
U.S. Appl. No. 13/266,049, filed Oct. 24, 2011, Stroefer, et al.
U.S. Appl. No. 13/380,680, filed Dec. 23, 2011, Schelling, et al.
U.S. Appl. No. 13/383,549, filed Jan. 11, 2012, Schelling, et al.
U.S. Appl. No. 13/479,961, filed May 24, 2012, Stroefer, et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The present invention relates to a process for preparing light-colored polyphenylene-polymethylene-polyisocyanate (PMDI), comprising the steps (a) providing carbon monoxide and chlorine, (b) reacting carbon monoxide with chlorine to form phosgene, (c) reacting the phosgene from step (b) with at least one primary amine with the exception of mono- and polyphenylene-polymethylene polyamines with an excess of phosgene to form an at least one isocyanate containing reaction solution, and hydrogen chloride, (d) separating excess phosgene from the isocyanate-containing reaction solution obtained in step (c), (e) providing at least one polyphenylene-polymethylene polyamine, and (f) reacting at least a portion of the phosgene separated in step (d) with the at least one polyphenylene-polymethylene polyamine to form the light-colored polyphenylene-polymethylene polyisocyanate.

20 Claims, 1 Drawing Sheet

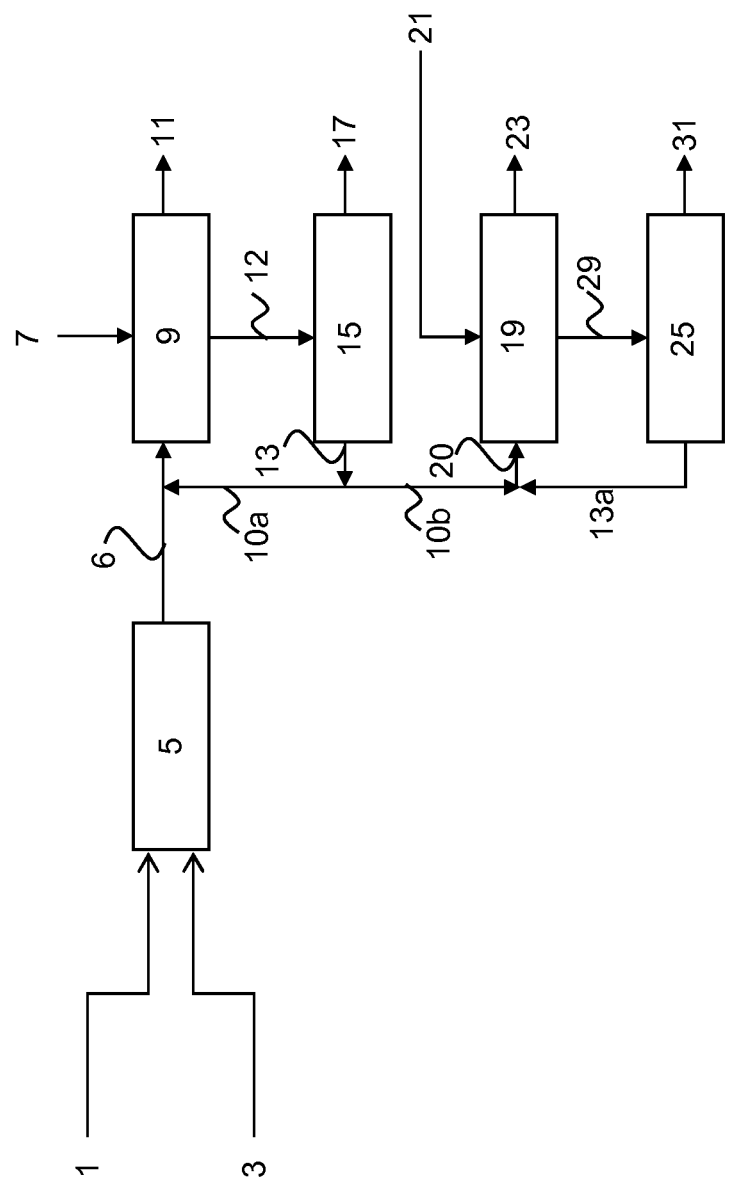

PROCESS FOR PREPARING LIGHT-COLOURED ISOCYANATES OF THE DIPHENYLMETHANE SERIES

This application is a 371 of PCT/EP2010/059684 filed Jul. 7, 2010; and claims benefit of U.S. provisional Application Ser. No. 61/225,376, filed Jul. 14, 2009.

The present invention relates to a process for preparing diisocyanates and polyisocyanates of the diphenylmethane series (MDI).

Isocyanates and isocyanate mixtures are prepared by known methods by phosgenation of the corresponding amines. For polyurethane foams, for example, bifunctional or polyfunctional aromatic isocyanates of the diphenylmethane diisocyanate series (MDI) are employed. Due to the production process, dark-coloured products are often obtained after the phosgenation and the subsequent work-up (removal of HCl, phosgene, solvent and monomeric MDI) and these in turn give yellowish polyurethane foams or other, likewise discoloured polyurethane materials. This is undesirable, since such coloration detracts from the overall visual impact and allows slight inhomogenities to occur, such as streaks in the foams obtained. Light-coloured isocyanates or isocyanates which contain a reduced amount of colour-imparting compounds are therefore preferred as raw materials.

Furthermore, the presence of bromine and of iodine reduces the yield due to byproduct formation. The removal of the by-products increases the outlay required for separation tasks. In addition, product of value is lost during the removal of the byproducts.

WO 01/00569 A1 discloses a process for preparing isocyanates which contain only small amounts, if any, of colour-imparting components, which leads, without further pretreatment or after-treatment steps, to light-coloured isocyanates which are suitable for producing polyurethanes having no colour or only a slight colour. In this process, phosgene containing less than 50 ppm of bromine or bromine-containing compounds or iodine or iodine-containing compounds is used in the preparation of the isocyanates.

Usually chloride is produced industrially from rock salt, sea salt or mined potassium chloride. Here, chlorine is usually produced together with sodium or sodium hydroxide as co-product by electrolysis of a rock salt solution. Potassium chloride is used analogously for the production of chlorine together with potassium or potassium hydroxide. The salts used in the electrolysis usually contain bromine, iodine and ammonia compounds in amounts of from 30 to 3000 ppm and these form bromine, iodine and $NCl_3$ during the electrolysis.

A disadvantage of the above desired process is the high cost of purification required to reduce the bromine and iodine content in the chlorine used for the phosgene synthesis to such an extent that the resulting phosgene to be used in isocyanate production has the necessary low content of bromine, iodine, bromine-containing or iodine-containing compounds.

EP-A 0 876 335 discloses a process for preparing isocyanates from phosgene and amines, in which the hydrogen chloride obtained in isocyanate production is oxidized electrolytically to produce chlorine. The chloride obtained is recycled to the phosgene synthesis. However, the electrolysis of hydrogen chloride is associated with high electricity costs. In addition, hydrogen is formed as co-product in this process, which can cause safety problems. In the above-mentioned document, it is stated that the electrolytically produced hydrogen is used for the production of amines for the corresponding nitro compounds. However, this advantage disappears if the isocyanate production is not back-integrated to the preparation of the amines from the corresponding nitro compounds. In any case, the hydrogen formed in the electrolysis of hydrogen chloride is not sufficient for the reduction of the nitro compounds. A further disadvantage is that even slight traces of organic compounds, for example solvent residues from isocyanate production, interfere in the sensitive hydrogen chloride electrolysis, so that the hydrogen chloride used has to be very pure.

The object of the invention is to provide a process for preparing light-coloured polyisocyanates of the diphenylmethane series (MDI), which works without further pretreatment or after-treatment steps for lightening the color of the polyisocyanates obtained and in which the need for purification of the raw materials used is minimum.

It has now been found, that this object is achieved by a process for preparing light-coloured polyphenylene-polymethylene-polyisocyanate (PMDI), comprising the steps (a) providing carbon monoxide and chlorine, (b) reacting carbon monoxide with chlorine to form phosgene, (c) reacting the phosgene from step (b) with at least one primary amine with the exception of mono- and polyphenylene-polymethylene polyamines with an excess of phosgene to form an at least one isocyanate containing reaction solution, and hydrogen chloride, (d) separating excess phosgene from the isocyanate-containing reaction solution obtained in step (c), (e) providing at least one polyphenylene-polymethylene polyamine, and (f) reacting at least a portion of the phosgene separated in step (d) with the at least one polyphenylene-polymethylene polyamine to form the light-coloured polyphenylene-polymethylene polyisocyanate.

The present inventors have discovered a significant advantage in reacting at least a portion from the excess phosgene of a first isocyanate synthesis in the synthesis of PMDI. The process of the present invention leads to PMDI isocyanates which can be used for preparing urethane compounds such as polyurethanes or their precursors which have no colour or only a slight colour. The result obtained according to the present invention was particularly surprising, because it had hereto not been recognized that the use of excess phosgene separated from an upstream isocyanate synthesis in the PMDI-synthesis allows obtaining light-coloured PMDI isocyanates.

Phosgene used for the preparation of isocyanates generally has a certain content of molecular or bound bromine or iodine or of the above-mentioned mixtures. The content of bromine or iodine or of such mixtures in the phosgene results from the chlorine used for preparing the phosgene, since the chlorine usually contains a certain proportion of bromine or iodine or both. The content of bromine or iodine or both in the chlorine generally results from the corresponding content in the salt used for producing the chlorine. The bromine or BrCl present in the chlorine leads to formation of dibromophosgene or bromochlorophosgene in the phosgene synthesis. These compounds are said to react similarly to phosgene with amines to form isocyanates and hydrogene bromide. Analogous reactions can be assumed for iodine.

The phosgene separated in step (d) of the process of the invention has a significantly low content of bromine or iodine or of the above-mentioned mixtures which is less than 50 ppm, in particular less than 10 ppm.

In step (a) an amount of carbon monoxide and chlorine are provided. The chlorine of this first amount may have a content of free and bound bromine and iodine. Bromine and iodine can be present in the chlorine in molecular (free) form as $Br_2$ or $I_2$ or also in bound form, for example as BrCl and ICl.

Processes for preparing appropriate chlorine having a content of bromine and iodine are known to those skilled in the art. In principle, it is possible to use any chlorine with a content of less than about 2000 ppm of bromine and iodine, for the purpose of the present invention. Thus, for example, it is possible to use chlorine which has been produced by electrolysis process or by oxidation of hydrogen chloride, e.g. by the Deacon process.

According to an embodiment of the invention, the chlorine is produced by electrolysis of a solution containing chloride ions. In general, this is an aqueous rock salt solution, an aqueous potassium chloride solution or aqueous hydrogen chloride (hydrochloric acid). Thus, the chlorine synthesis can be carried out using appropriate starting materials which themselves have a low bromine and iodine content, e.g. low-bromine and low-iodine salts or low-bromine and low-iodine hydrochloric acid. Such low bromine and low iodine salts having a total bromine and iodine content of <400 ppm are mined, for example, at Heilbronn, Germany.

The preparation of chlorine having a particularly low bromine content can also be carried out, as described in U.S. Pat. No. 3,660,261, by oxidative treatment of the salt used for the electrolysis.

According to a preferred embodiment of the invention, the chlorine provided in step (a) of the inventive process contains less than 1000 ppm, preferably contains less than 500 ppm of bromine and iodine.

In step (b) chlorine is reacted with carbon monoxide to form phosgene. Methods of preparing phosgene are described e.g. in Ullmanns Enzyklopädie der industriellen Chemie, 3rd edition, volume 13, pages 494 to 500. Thus, phosgene can be obtained by passing carbon monoxide and chlorine over actuated carbon. In one particularly preferred embodiment of the invention, the reaction of carbon monoxide with chlorine to form phosgene in step (b) is carried out using activated carbon as a catalyst in a fixed bed reactor with a slight molar excess of CO (about 0.5 to 15 mol % stoichiometrically) at a temperature of about 20 to 600° C. and a pressure of about 1 to 20 bar. Operating under pressure can allow the size of the reaction vessel to be reduced.

In step (c) an excess of the phosgene from step (b) is reacted with at least one primary amine with the exception of mono- and polyphenylene-polymethylene polyamines, to form the corresponding isocyanates and hydrogene chloride. This reaction is also referred to as phosgenation of the amines. Amines used in step (c) have at least one primary amino group, preferably two primary amino groups and possibly also three or more primary amino groups and are different from mono- and polyphenylene-polymethylene polyamines.

The preparation of isocyanates in step (c) is carried out in a manner known to those skilled in the art by reacting an amine or a mixture of two or more amines with an excess, that means a super stoichiometric amount, of phosgene. It is in principle possible to employ all processes in which a primary amine or a mixture of two or more primary amines having one or more primary amino groups with phosgene to form one or more isocyanates having one or more isocyanate groups.

According to a preferred embodiment of the invention, the phosgenation of the amine or amines in step (c) is carried out in a solvent or a solvent mixture. As solvent, it is possible to use all solvents suitable for the preparation of isocyanates. These are preferably inert aromatic, aliphatic or alicyclic hydrocarbons or their halogenated derivatives. Examples of such solvents are aromatic compounds such as monochlorobenzene or dichlorobenzene, for example o-dichlorobenzene, toluene, xylenes, naphthalene derivatives such as tetralin or decalin, alkanes having from about 5 to about 12 carbon atoms, e.g. hexane, heptane, octane, nonane or decane, cycloalkanes such as cyclohexane, effectively inert esters and ethers such as ethyl acetate or butyl acetate, tetrahydrofuran, dioxane or diphenyl ether.

Suitable amines used in step (c) are in principle all primary amines which can react in an appropriate manner with phosgene to form isocyanates, with the provision that mono- and polyphenylene-polymethylene amines are excluded. The amines reacted in step (c) may be linear or branched saturated or unsaturated aliphatic or cycloaliphatic or aromatic primary monoamines which can be reacted with phosgene to give isocyanates.

Examples of useful amines are 1,3-propylenediamine, 1,4-butylenediamine, 1,5-pentamethylenediamine, 1,6-hexamethylenediamine and their corresponding higher homologues in the series, isophoronediamine (IPDA), cyclohexylenediamine, cyclohexylamine, anilline, phenylendiamine, p-toluidine, 1,5-naphthylenediamine, 2,4- or 2,6-toluenediamine or mixtures thereof.

The reaction (c) of the phosgene with the above-mentioned amines can be carried out continuously or batchwise in one or more stages. The reaction is usually carried out at a temperature of from about 40 to 200° C.

In step (d) HCl and excess phosgene are separated off from the isocyanate-containing reaction solution obtained in step (c).

The phosgene excess in step (c) depends from the amine used. Usually, the excess of phosgene should be at least 100% of the stoichiometric amount, and preferably at least 1500% of the stoichiometric amount. The excess phosgene can be separated from the isocyanate-containing reaction solution by at least one operation selected from liquefacation or condensation of the phosgene, distillation or rectification and/or scrubbing of the phosgene with a solvent, such as e.g. monochlorbenzene or orthochlorbenzene. Separation of the phosgene by condensation or distillation is preferred. The excess phosgene can be removed at a temperature of from 50 to 180° C.

According to the invention, the excess phosgene separated in step (d) is returned/fed to a further phosgenation reaction and at least a portion of the phosgene separated in step (d) is reacted with at least one polyphenylene-polymethylene polyamine to form the corresponding polyphenylene polymethylene polyisocyanate (PMDI) in reaction step (f). For this case, at least one polyphenylene-polymethylene polyamine is provided in step (e).

Since the phosgene separated off in step (d) has already gone through step (c), an isocyanate synthesis, this phosgene will in any case have a significantly lower bromine and iodine content than the phosgene formed in step (b).

The excess phosgene separated in step (d) of the method of the invention is substantially free from residual bromine and iodine phosgene, usually below 100 ppm. Thus, the isocyanate obtained in step (c) of the inventive method is "contaminated" with relatively high bromine and iodine contents, while the isocyanate, the polyphenylene-polymethylene polyisocyanate (PMDI) prepared in the later step (f) has only come into contact with the very much lower bromine and iodine containing phosgene. Hence, the invention provides an efficient process for preparing light-coloured polyphenylene-polymethylene polyisocyanates (PMDI) without further pretreatment or after-treatment steps for lightening the colour of the PMDI-isocyanates obtained in step (f).

In step (e) at least one primary diphenylmethane diamine (MDA) or their oligomeric or polymeric derivatives, i.e. the amines of the diphenylmethane diamine series is provided. Diphenylmethane diamine, its oligomers or polymers are obtained, for example, by condensation of aniline with formaldehyde. Such oligoamines or polyamines or their mixtures are also provided in step (e) in a preferred embodiment of the invention.

The reaction (f) of the low-bromine and low-iodine phosgene with the above-mentioned diphenylmethane diamine(s) (MDA) can be carried out continuously or batchwise in one or more stages. If a single stage reaction is carried out, this is preferably carried out at a temperature of from about 40 to 200° C., for example at from about 70 to 180° C.

In a further embodiment of the invention, super-atmospheric pressure, generally up to 100 bar or less, preferably of from 1 bar to about 50 bar, particularly preferably from 2 bar to 25 bar, can be applied during the reaction (f). In a further embodiment of the invention, the reaction is carried out at about 1 bar (ambient pressure). In a further embodiment, a pressure below ambient pressure is employed.

In a subsequent step (g), the polyphenylene polymethylene polyisocyanate (PMDI) formed are separated off from the reaction mixture and, if necessary, purified.

The preparation of PMDI isocyanates in step (f) in the process of the present invention is carried in a manner known to those skilled in the art by reacting at least one amine provided in step (e) with a (super-stoichiometric) amount of phosgene. It is in principle possible to employ all processes in which a primary amine or a mixture of two or more primary amines are reacted with phosgene to form one or more isocyanates of the PMDI group.

In the preferred embodiment of the invention, the reaction of the phosgene and the amine or amines in step (f) is carried out in a solvent or a solvent mixture. As solvent it is possible to use all abovementioned solvents suitable for the preparation of isocyanates.

The process of the present invention is explained in more detail below with reference to the FIGURE by way of the example.

BRIEF DESCRIPTION OF THE DRAWING

In FIG. 1 an example of the process of the present invention is illustrated diagrammatically.

In FIG. 1 a stream of chlorine 1 and a stream of carbon monoxide 3 are fed into the phosgene synthesis stage 5 and are there reacted to form phosgene, with carbon monoxide preferably being used in excess. The resulting phosgene stream 6 also contains proportions of bromine and iodine present in the chlorine used. These can be present both in molecular form and in chemically bound form (e.g. as bromophosgene). This stream 6, a stream 7 comprising solvent and amine with the exception of polyphenylene-polymethylene-polyamines and optionally a phosgene recycled stream 10a are fed into the phosgenation stage 9 where the reaction of amine with phosgene to form isocyanate and hydrogen chloride takes place. The phosgenation stage 9 can be configured as, for example, a stirred vessel, a cascade of stirred vessels, a reaction column or a tube reactor with upstream mixing device or as a combination of the above-mentioned apparatuses. The phosgenation can be carried out in two stages as a cold phosgenation with subsequent hot phosgenation. This gives a product stream 11 comprising solvent, isocyanate and by-products (e.g. urea, oligomers) from which the solvent is separated off in a subsequent separation stage, preferably by distillation. Hydrogen chloride formed in the phosgenation reaction and excess phosgene leaves the phosgenation stage 9 as gas stream 12 which may further comprise solvent residues, low-boiling by-products, carbon monoxide, carbon dioxide and inert gases (for example nitrogen, argon).

Phosgene and solvent residues are separated off from this gas stream 12 in the separation stage 15, preferably by distillation, and are recirculated as recycled stream 13 which is divided into stream 10a which is fed to the phosgenation stage 9 and into stream 10b which is fed into a subsequent phosgenation stage 19. A hydrogen chloride stream 17 leaves the separation stage 15 which may still contain traces of solvent, phosgene or inerts. At least a portion 10b of the recycled stream 13 which consists essentially of phosgene and which has a significantly low content of bromine or iodine of less than 50 ppm, in particular less than 10 ppm, and a stream 21 comprising a solvent and at least one amine of the polyphenylene-polymethylene-polyamine series are fed into the phosgenation stage 19 where the reaction of the polyphenylene-polymethylene-polyamine with phosgene to form a light-coloured polyphenylene-polymethylene polyisocyanate and hydrogen chloride takes place. The phosgenation stage 19 can be configured as, for example, a stirred vessel, a cascade of stirred vessels, a reaction column or a tube reactor with upstream mixing device or as a combination of the above-mentioned apparatuses. Phosgenation can be carried out in two stages as a cold phosgenation with subsequent hot phosgenation. This gives a liquid product stream 23 comprising solvent, PMDI isocyanates and byproducts (e.g. urea, oligomers) from which the solvent is separated off in a subsequent separation stage, preferably by distillation. Hydrogen chloride formed in the phosgenation reactions and excess phosgene leave the phosgenation stage 19 as gas stream 29 which may further comprise solvent residues, low-boiling by-products, carbon monoxide, carbon dioxide and inert gases (for example nitrogen, argon). Phosgene and solvent residues are separated off from this in the separation stage 25, preferably by distillation and are re-circulated as recirculated stream 13a to the phosgenation stage 9 and/or 19. The separation stage 25 leaves further a hydrogen chloride stream 31 which may still contain traces of solvent, phosgene and inerts.

We claim:

1. A process for preparing a polyphenylene-polymethylene polyisocyanate, the process comprising:
    (a) reacting carbon monoxide with chlorine to form phosgene;
    (b) reacting phosgene from (a), in an excess, with at least one primary amine excluding mono- and polyphenylene-polymethylenepolyamines, to form at least one first reaction solution comprising an isocyanate, and hydrogen chloride;
    (c) separating excess phosgene from the first reaction solution; and
    (d) reacting at least a portion of the phosgene separated in (c) with at least one polyphenylene-polymethylenepolyamine to form a second reaction solution comprising a polyphenylene-polymethylene polyisocyanate.

2. The process of claim 1, wherein the primary amine is at least one selected from the group consisting of 1,3-propylenediamine, 1,4-butylenediamine, 1,5-pentamethylenediamine, 1,6-hexamethylenediamine and corresponding higher polyalkylene diamine homologues, isophoronediamine, cyclohexylenediamine, cyclohexylamine, aniline, phenylenediamine, p-toluidine, 1,5-naphthylenediamine, 2,4-toluenediamine, and 2,6-toluenediamine.

3. The process of claim 1, wherein the separating (c) comprises performing at least one operation selected from the group consisting of liquefying the excess phosgene, condensing the excess phosgene, rectifying the excess phosgene, distilling the excess phosgene, and scrubbing the excess phosgene with a solvent.

4. The process of claim 1, wherein the reacting (b) is carried out in a solvent.

5. The process of claim 1, wherein the reacting (d) is carried out in a solvent.

6. The process of claim 1, wherein the reacting in (b) and (d) is carried out in a solvent, and wherein the solvent in (b) and (d) is the same.

7. The process of claim 4, wherein the solvent is at least one selected from the group consisting of o-dichlorobenzene, toluene, xylene, tetralin, decalin, hexane, heptane, octane, nonane, decane, cyclohexane, ethyl acetate, butyl acetate, tetrahydrofuran, dioxane, and diphenyl ether.

8. The process of claim 1, wherein at least one selected from the group consisting of the reacting (b) and the reacting (d) is carried out under super-atmospheric or atmospheric pressure.

9. The process of claim 1, wherein the phosgene in (b) is in a stoichiometric excess of at least 100%.

10. The process of claim 1, wherein the chlorine has a bromine and iodine content of less than 1000 ppm.

11. The process of claim 1, wherein the chlorine has a bromine and iodine content of less than 500 ppm.

12. The process of claim 1, wherein the reacting (b) is carried out continuously at a temperature of from 40 to 200° C.

13. The process of claim 1, wherein phosgene in (b) is in a stoichiometric excess of at least 1500%.

14. The process of claim 1, wherein the separating (c) is carried out at a temperature of from 50 to 180° C.

15. The process of claim 1, wherein the separating (c) comprises distilling the excess phosgene.

16. The process of claim 1, wherein the separating (c) comprises condensing the excess phosgene.

17. The process of claim 1, further comprising:
    (e) separating excess phosgene from the second reaction solution.

18. The process of claim 17, wherein the separating (e) comprises distilling the excess phosgene.

19. The process of claim 17, further comprising:
    (f) recirculating the excess of phosgene separated in (e) to at least one selected from the group consisting of the reacting (b) and the reacting (d).

20. The process of claim 1, wherein the reacting (d) is carried out continuously at a temperature in of from 70 to 180° C.

* * * * *